US012133633B2

(12) United States Patent
Crawford et al.

(10) Patent No.: US 12,133,633 B2
(45) Date of Patent: Nov. 5, 2024

(54) DISTAL TIPS FOR MEDICAL DEVICES

(71) Applicant: Boston Scientific Scimed, Inc., Maple Grove, MN (US)

(72) Inventors: Richard Crawford, Galway (IE); Martin Fawdry, Galway (IE); Ben McNicholl, Lisburn (IE); Aiden Flanagan, Kilcolgan (IE); Elizabeth Albrecht, White Bear Lake, MN (US); Leili Salehi, Waltham, MA (US); Anne Gu, Waltham, MA (US); Bryan Clark, Forest Lake, MN (US); Megan Chrobak, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 120 days.

(21) Appl. No.: 17/226,152

(22) Filed: Apr. 9, 2021

(65) Prior Publication Data
US 2021/0315446 A1    Oct. 14, 2021

Related U.S. Application Data

(60) Provisional application No. 63/008,152, filed on Apr. 10, 2020.

(51) Int. Cl.
*A61B 1/00* (2006.01)
*A61B 1/005* (2006.01)
(Continued)

(52) U.S. Cl.
CPC .......... *A61B 1/018* (2013.01); *A61B 1/00091* (2013.01); *A61B 1/00101* (2013.01);
(Continued)

(58) Field of Classification Search
CPC . A61B 1/018; A61B 1/00091; A61B 1/00101; A61B 1/0057; A61B 1/05;
(Continued)

(56) References Cited

U.S. PATENT DOCUMENTS 3,143,595 A * 8/1964 Martin ................. H01R 4/72
                                                              174/90
4,151,364 A * 4/1979 Ellis .................. B29C 61/003
                                                         174/DIG. 8

(Continued)

FOREIGN PATENT DOCUMENTS

EP        3539453       9/2019

OTHER PUBLICATIONS

International Search Report and Written Opinion issued in International Application No. PCT/US2021/026512, issued Jul. 1, 2021 (11 pages).

*Primary Examiner* — Timothy J Neal
(74) *Attorney, Agent, or Firm* — Bookoff McAndrews, PLLC

(57) ABSTRACT

A medical device may comprise a distal tip having a viewing element, a lighting element, and at least one feature configured to removably couple the distal tip to a shaft. The medical device may also comprise a working channel coupled to the distal tip and defining a central lumen configured to receive a tool. A wall of the working channel may define at least one additional lumen. The working channel may be configured to be removably inserted into the shaft. The medical device may also comprise at least one of a wire, a cable, or a conduit passing through the at least one additional lumen.

13 Claims, 11 Drawing Sheets

(51) Int. Cl.
   *A61B 1/018*   (2006.01)
   *A61B 1/05*    (2006.01)
   *A61B 1/06*    (2006.01)

(52) U.S. Cl.
   CPC .............. *A61B 1/0057* (2013.01); *A61B 1/05* (2013.01); *A61B 1/0676* (2013.01)

(58) Field of Classification Search
   CPC .............. A61B 1/0676; A61B 1/00103; A61B 1/00128; A61B 1/00137; A61B 1/0014; A61B 1/00142; A61B 1/00172; A61B 1/00177; A61B 1/0125; A61B 1/053; A61B 1/0684; A61B 1/00098
   See application file for complete search history.

(56) References Cited

U.S. PATENT DOCUMENTS

| | | | | |
|---|---|---|---|---|
| 5,569,157 | A * | 10/1996 | Nakazawa | A61B 1/00177 |
| | | | | 600/106 |
| 6,059,719 | A * | 5/2000 | Yamamoto | A61B 17/00234 |
| | | | | 606/1 |
| 6,921,362 | B2 * | 7/2005 | Ouchi | A61B 1/018 |
| | | | | 600/125 |
| 2007/0208220 | A1 * | 9/2007 | Carter | A61B 1/00098 |
| | | | | 604/165.01 |
| 2007/0265499 | A1 * | 11/2007 | Wood | A61B 1/00181 |
| | | | | 600/137 |
| 2008/0058595 | A1 * | 3/2008 | Snoke | A61B 1/00135 |
| | | | | 600/114 |
| 2008/0262302 | A1 * | 10/2008 | Azarbarzin | A61B 1/018 |
| | | | | 604/93.01 |
| 2009/0231419 | A1 | 9/2009 | Bayer | |
| 2012/0016191 | A1 * | 1/2012 | Ito | A61B 1/0051 |
| | | | | 600/104 |
| 2013/0172670 | A1 * | 7/2013 | Levy | A61B 1/053 |
| | | | | 600/110 |
| 2013/0261391 | A1 * | 10/2013 | Dejima | A61B 1/0016 |
| | | | | 600/114 |
| 2014/0343358 | A1 | 11/2014 | Hameed et al. | |
| 2016/0000455 | A1 * | 1/2016 | Golan | A61B 18/1492 |
| | | | | 606/41 |
| 2016/0183914 | A1 * | 6/2016 | Fujimura | A61B 8/4444 |
| | | | | 600/459 |
| 2018/0206708 | A1 * | 7/2018 | Miller | A61B 1/01 |
| 2018/0333044 | A1 * | 11/2018 | Jenkins | A61B 1/00059 |
| 2021/0093160 | A1 * | 4/2021 | Eastwood | A61B 1/0055 |
| 2021/0228146 | A1 * | 7/2021 | Batchelor | A61B 5/742 |

* cited by examiner

DISTAL TIPS FOR MEDICAL DEVICES

CROSS-REFERENCE TO RELATED APPLICATIONS

This present disclosure claims priority to U.S. Provisional Patent Application No. 63/008,152, filed on Apr. 10, 2020, the disclosure of which is incorporated herewith by reference.

TECHNICAL FIELD

The disclosure relates generally to elements of medical devices. Aspects of the disclosure pertain to devices, systems, and/or methods for distal tips of endoscopic devices.

BACKGROUND

Duodenoscopes may include a handle portion, which may be gripped by an operator and may include control elements for functions such as steering, suction, water, air, light, and imaging. A duodenoscope may also include a portion which may be inserted into a subject. For example, a duodenoscope may include a shaft suitable for insertion into a subject. Such an insertion portion may include one or more lumens. The lumens of an insertable portion of a duodenoscope may support the functions, for example, conveying air, water, suction, electricity, data, light, and/or images. Tools may also be inserted via a working channel of the shaft. For example, a tool may be inserted by a port in or near the handle of a duodenoscope into the working channel.

A shaft of a duodenoscope may terminate in a steerable distal portion. A distal portion of a duodenoscope may include outlets for air, water, suction, electricity, data, light, images, and/or working tools from lumen(s) of a duodenoscope. Components of the distal tip may be subjected to fluids or other substances of a body lumen of the subject. Before reuse with another patient, the duodenoscope may be subject to reprocessing procedures.

SUMMARY

Examples of the disclosure relate to, among other things, devices, systems, and methods for distal tips of medical devices. Each of the examples disclosed herein may include one or more of the features described in connection with the disclosed examples.

In one example, a medical device may comprise a distal tip having a viewing element, a lighting element, and at least one feature configured to removably couple the distal tip to a shaft. The medical device may also comprise a working channel coupled to the distal tip and defining a central lumen configured to receive a tool. A wall of the working channel may define at least one additional lumen. The working channel may be configured to be removably inserted into the shaft. The medical device may also comprise at least one of a wire, a cable, or a conduit passing through the at least one additional lumen.

Any of the medical devices disclosed herein may have any of the following features. The at least one of the wire, the cable, or the conduit may include the wire or the cable. The wire or the cable may be configured to operate at least one of an elevator of the distal tip, the viewing element, or the lighting element. The distal tip may further include a motor operative to raise or lower the elevator. The at least one of the wire, the cable, or the conduit may include the wire or the cable. The wire or the cable may be configured to provide power to the motor. The wall of the working channel may define at least two additional lumens. The distal tip may have a post extending from a proximal surface thereof. The post may be configured to be detachably connected to a control wire extending through the shaft. The post may define at least one slot, and the control wire may include at least one protrusion configured to be received by the at least one slot. The distal tip may have at least one peg extending from a proximal surface thereof. The peg may be configured to couple the distal tip to the shaft. The distal tip may be configured to be rotatable relative to the shaft. The distal tip may include a motor configured to rotate the distal tip relative to the shaft. The motor may be configured to rotate a gear. The distal tip may include teeth configured to engage with the gear. The distal tip may include a magnet for coupling an element of the distal tip to an element of the shaft. The distal tip may further comprise a distal tip elevator control wire for raising and lowering an elevator of the endoscope. A proximal end of the elevator control wire may include a notch configured to mate with a slot of a shaft elevator control wire. A proximal end of the working channel may include a plurality of threads for securing the proximal end to a handle at a proximal end of the shaft. A proximal end of the distal tip may define a port for operatively connecting an electronic element of the distal tip to a shaft cable or wire extending through the shaft.

In another example, a medical device may comprise: a distal tip having a viewing element, a lighting element, and a nozzle. A working channel may be coupled to the distal tip and define a central lumen configured to receive a tool. A wall of the working channel may define at least one additional lumen. The working channel may be configured to be removably inserted into the shaft. The at least one additional lumen may be configured to be in fluid communication with the nozzle.

Any of the medical devices disclosed herein may have any of the following features. The distal tip may further include a motor operative to raise or lower the elevator. The at least one of the wire, the cable, or the conduit includes the wire or the cable, and wherein the wire or the cable is configured to provide power to the motor.

An example method may comprise: detachably coupling a distal tip to a shaft of a medical device. The distal tip may have: a viewing element, and a lighting element. The method may further comprise feeding a working channel through the shaft and detachably coupling the working channel to a handle of the medical device.

Any of the methods disclosed herein may have any of the following features. The working channel may define a central lumen configured to receive a tool. A wall of the working channel may define at least one additional lumen. At least one of a wire, a cable, or a conduit may pass through at least one additional lumen. The at least one of the wire, the cable, or the conduit may be configured to be operatively connected to at least one of the elevator, the viewing element, the lighting element, or the nozzle.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

The term "distal" refers to a direction away from an operator/toward a treatment site, and the term "proximal" refers to a direction toward an operator. The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate examples of the disclosure and together with the description, serve to explain the principles of the disclosure.

DETAILED DESCRIPTION

During reprocessing, it may be difficult to sufficiently clean a distal tip of a duodenoscope and/or a working channel of a duodenoscope. Therefore, it may be desirable for a distal tip of a duodenoscope and/or a working channel be removable from a remainder of the duodenoscope. The distal tip and/or the working channel may be disposable in order to obviate a need to reprocess the distal tip and/or working channel. The distal tip and/or a shaft of the duodenoscope may include features to facilitate connections between elements of the distal tip (e.g., an elevator, air/water nozzle, viewing element, and/or lighting element) and elements in the shaft and handle of the duodenoscope for controlling the elements of the distal tip. The distal tip may also have rotatable elements to allow rotation of the distal tip relative to the shaft of the duodenoscope.

Figure 1:
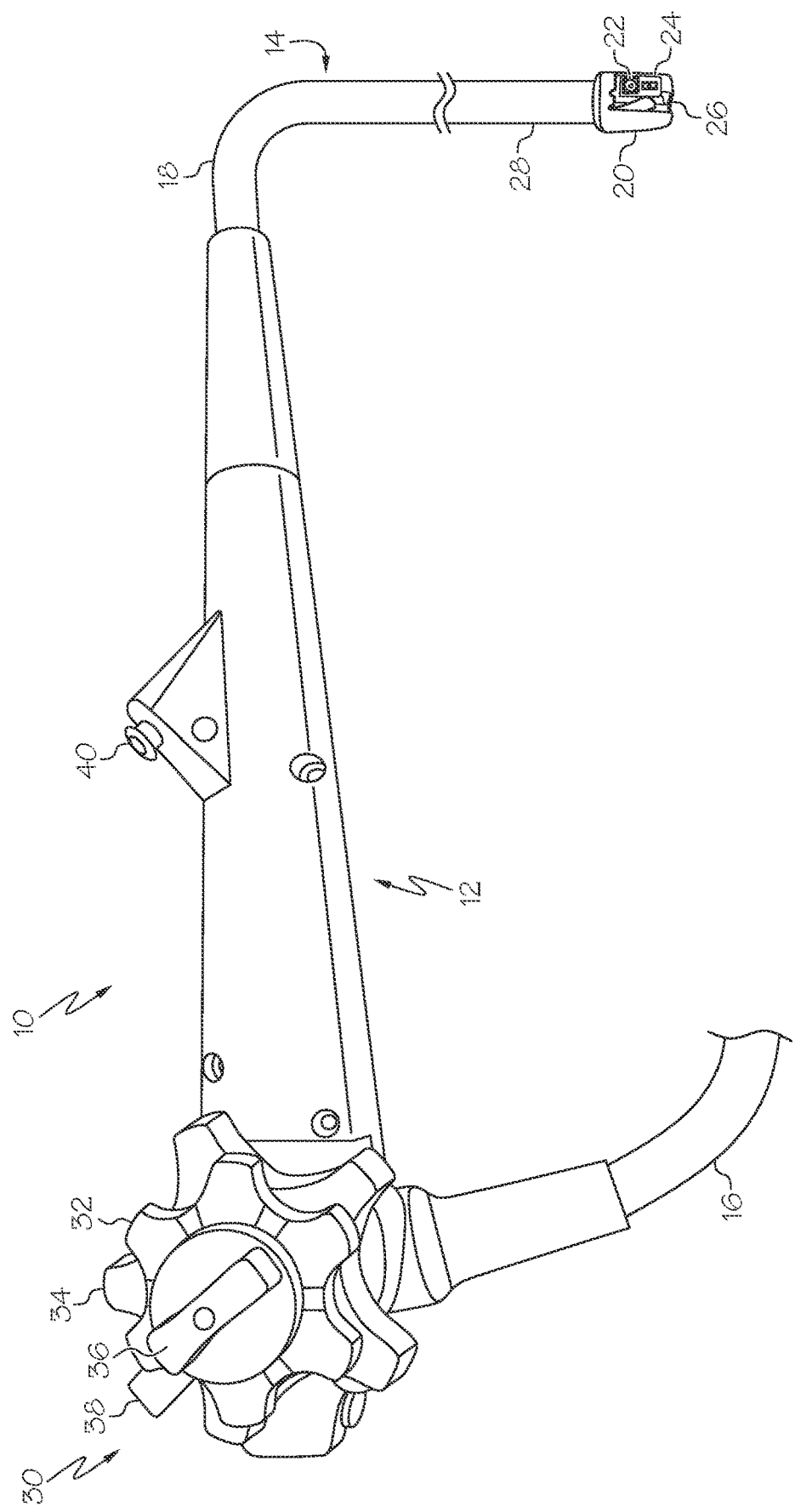
FIG. 1 depicts an exemplary duodenoscope.

FIG. 1 depicts an exemplary duodenoscope 10 having a handle 12 and an insertion portion 14. Duodenoscope 10 may also include an umbilicus 16 for purposes of connecting duodenoscope 10 to sources of, for example, air, water, suction, power, etc., as well as to image processing and/or viewing equipment. Although the term duodenoscope may be used herein, it will be appreciated that other devices, including, but not limited to, endoscopes, colonoscopes, ureteroscopes, bronchoscopes, laparoscopes, sheaths, catheters, or any other suitable delivery device or medical device may be used in connection with the coupling devices and methods of this disclosure. Although side-facing devices are particularly discussed, the embodiments described herein may also be used with front-facing endoscopes (e.g., endoscopes where a viewing element faces longitudinally forward).

Insertion portion 14 may include a sheath or shaft 18 and a distal tip 20. Distal tip 20 may include an imaging device (e.g., a camera) 22 and a lighting source 24 (e.g., an LED or an optical fiber). Distal tip 20 may also include an elevator 26 for changing an orientation of a tool inserted in a working channel of the duodenoscope 10 (further details about insertion of a tool are provided below). Elevator 26 may be pivotable via, e.g., an actuation wire. Distal tip 20 may be side-facing. That is, imaging device 22 and lighting source 24 may face radially outward, perpendicularly or approximately perpendicularly to a longitudinal axis of shaft 18 and distal tip 20.

A distal portion of shaft 18 that is connected to distal tip 20 may have a steerable section 28. Steerable section 28 may be, for example, an articulation joint. Shaft 18 and steerable section 28 may include a variety of structures which are known or may become known in the art. Example features of distal tip 20 are described in further detail with respect to FIGS. 2A-7C, herein.

Handle 12 may have one or more control mechanisms 30. Control mechanisms 30 may provide control over steerable section 28 or may allow for provision of air, water, suction, etc. For example, handle 12 may include control knobs 32, 34 for left, right, up, and/or down control of steerable section 28. For example, one of knobs 32, 34 may provide left/right control of steerable section 28, and the other of knobs 32, 34 may provide up/down control of steerable section 28. Handle 12 may further include one or more locking mechanisms 36 (e.g., knobs or levers) for preventing steering of steerable section 28 in at least one of an up, down, left, or right direction. Handle 12 may include an elevator control lever 38. Elevator control lever 38 may raise and/or lower elevator 20. A port 40 may allow passage of a tool through port 40, into a working channel of the duodenoscope 10, through sheath 18, to distal tip 20.

In use, an operator may insert at least a portion of shaft 18 into a body lumen of a subject. Distal tip 20 may be navigated to a procedure site in the body lumen. The operator may insert a tool (not shown) into port 40, and pass the tool through shaft 18 via a working channel to distal tip 20. The tool may exit the working channel at distal tip 20. The user may use elevator control lever 38 to raise elevator 26 and angle the tool toward a desired location (e.g., a papilla of the pancreatico-biliary tract). The user may use the tool to perform a medical procedure.

Figure 2A:
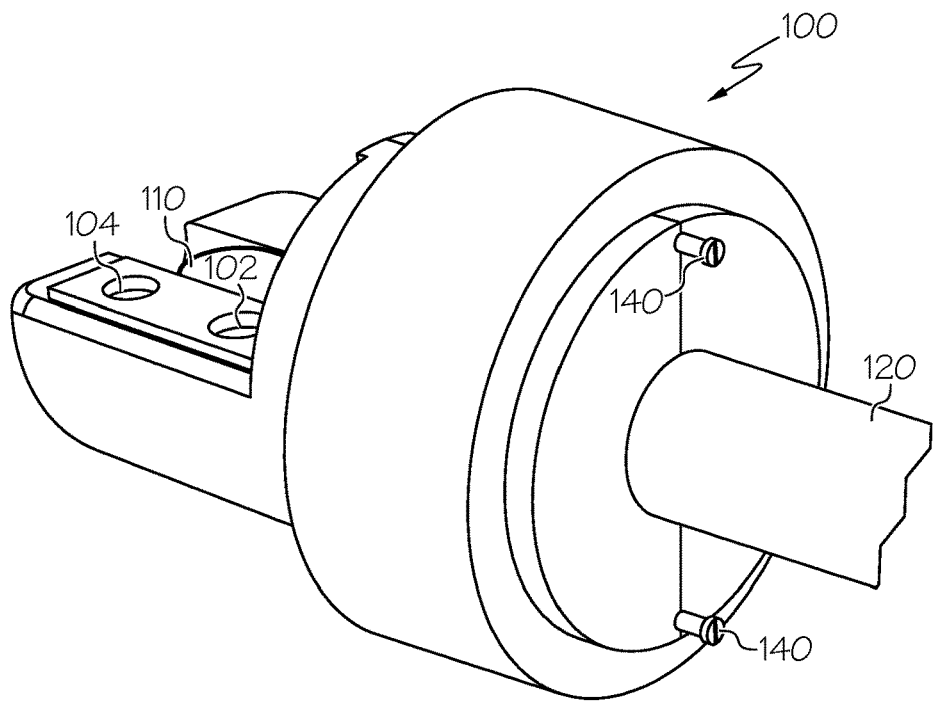
FIGS. 2A and 2B depict an exemplary distal tip for a duodenoscope.
Figure 2B:
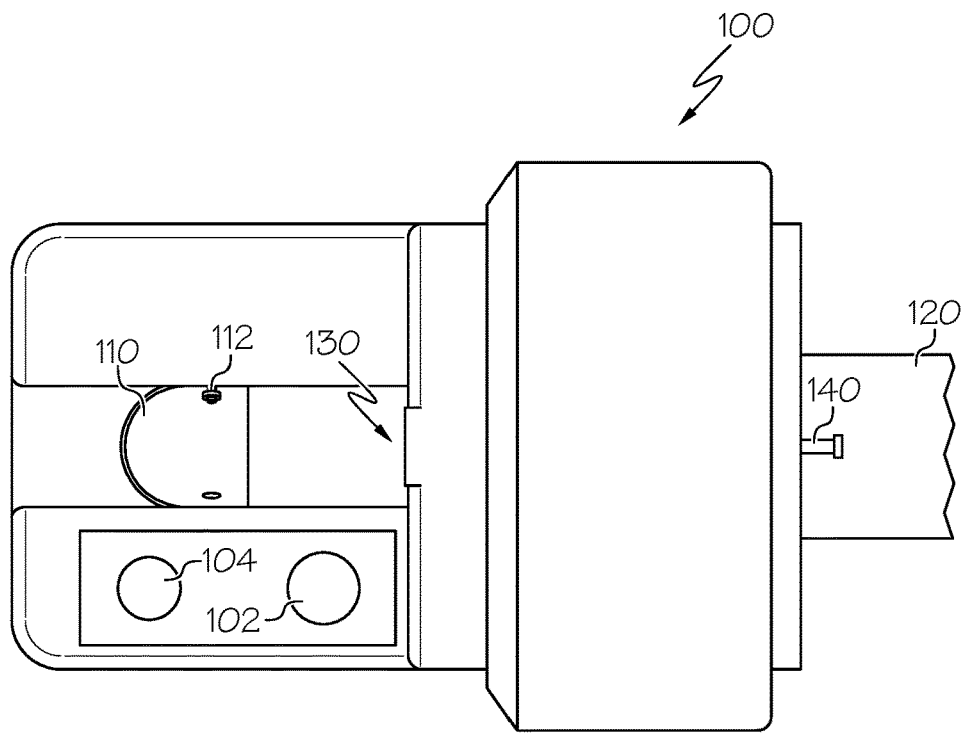

FIGS. 2A and 2B provide different views of an exemplary distal tip 100. FIG. 2A provides a perspective view, while FIG. 2B provides a profile view. Distal tip 100 may be used in place of distal tip 20 of duodenoscope 10, and may have any of the properties of distal tip 20. Distal tip 100 may be disposable. Distal tip 100 may be positioned on shaft 18 prior to use of duodenoscope 10 and removed from shaft 18 after use. Distal tip 100 may be disposed, and other portions of duodenoscope 10 may be reprocessed.

Distal tip 100 may include features including the following: viewing element 102 (e.g., a camera), lighting source 104, air and/or water nozzle(s), and/or elevator 110. Elevator 110 may have any of the properties of elevator 20. Elevator 110 may include an attachment point 112 for connecting elevator 110 to a mechanism for raising and/or lowering elevator 110 (e.g., a wire or a motorized element, as described below). Viewing element 102 may have any of the properties of viewing element 22. Viewing element 102 may include, for example, a charge coupled device ("CCD") unit, an image sensor, and/or an objective lens. Lighting source 104 may have any of the properties of lighting source 24. Lighting source 104 may include, for example, LED(s) or optical fiber(s). Distal tip 100 may also include internal components such as a motor and/or gears for rotation of distal tip 100 (see FIGS. 6A-7C, described below). Distal tip 100 may also house a motor for raising and lowering elevator 110, as described further with respect to FIGS. 6A-6B.

A working channel 120 may extend from a proximal end of distal tip 100. Working channel 120 may define a lumen (e.g., a central lumen) for receiving tools, delivering suction, and/or receiving body fluids or tissues. Working channel 120 may be detachable from distal tip 100 or may be fixedly coupled to distal tip 100. Working channel 120 may extend proximally from distal tip 100 to handle 12. When distal tip 100 is attached to a distal end of the duodenoscope, working channel 120 may be backfed through shaft 18, to handle 12. In handle 12, working channel 120 may be affixed to an appropriate structure (e.g., among others, instrument port 40). As discussed below, walls of working channel 120 may house a variety of components, such as wires and/or cables for viewing elements 102, lighting elements 104, and/or motors for rotation of distal tip 100 or operation of elevator 110. Working channel 120 may also house conduits in fluid communication with the air and/or water nozzles and/or a control mechanism (e.g., a wire) for elevator 110.

Distal tip 100 may house complementary components that are either one piece with the components of working channel 120 (e.g., in the case of a working channel 120 fixedly attached to distal tip 100) or that are separate components that are operatively connected/connectable to the components of working channel 120. Wires and/or cables, conduits, and elevator control elements may exist in each of handle 12, shaft 18, and distal tip 100 and may include single, unitary pieces or pieces that are operatively coupled to one another.

A lumen may extend through working channel 120, and the lumen may allow instruments, suction, and/or body tissue to be passed therethrough. Working channel 120 may terminate at a proximal end of distal tip 100 or within distal tip 100. The lumen of working channel 120 may be in communication with an opening 130 of the distal tip. The lumen of working channel 120 may terminate at opening 130, or structures of distal tip 100 (e.g., walls of distal tip 100) may form a channel in communication with the lumen of working channel 120. An instrument may be passed through the lumen of the working channel 120 and out of opening 130. Elevator 110 may be activated by elevator control lever 28 in order to raise or lower in order to change an orientation of the instrument extending out of opening 130.

A proximal side of distal tip 110 may include one or more mating components 140. As shown in FIG. 2A, distal tip 110 may have two mating components 140. Mating components 140 may include a variety of structures, such as those described below with respect to FIGS. 4A-4C. As shown in FIG. 2A, mating component 140 may include a protrusion (e.g., a peg) extending proximally from a proximal surface of distal tip 100. Mating component 140 may include a post and a head. Mating component 140 may have, for example, a shape like a head of a screw. Mating component 140 may mate with a component of shaft 18 of the duodenoscope or otherwise secure distal tip 100 to shaft 18. For example, a distal face of shaft 18 may include curved slots (not shown) for receiving mating components 140. Rotation of distal tip 100 relative to shaft 18 may cause mating components 140 to engage with the slots and to secure distal tip 100 to shaft 18. Alternatively, a distal face of shaft 18 may include openings that have round or other shapes for receiving and engaging with components 140 in order to secure distal tip 100 to shaft 18. Further details regarding example mating mechanisms will be provided below.

Figure 3:
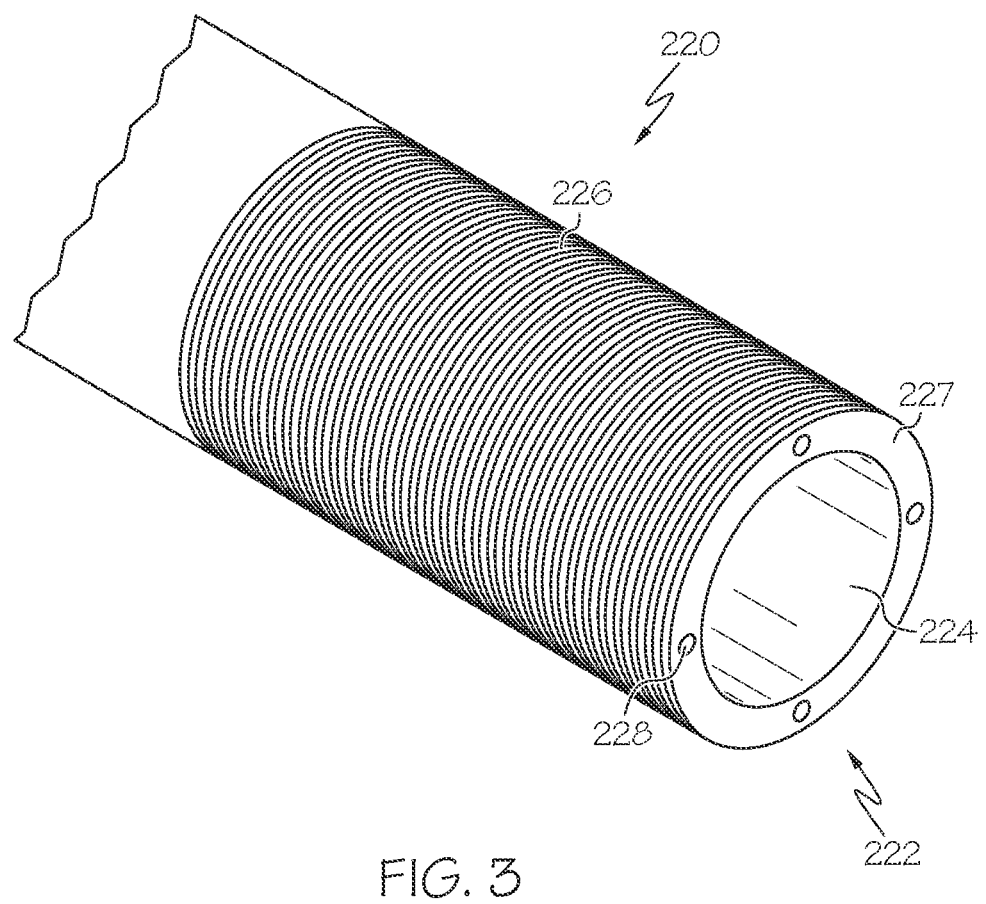
FIG. 3 depicts an exemplary working channel for use with the distal tip of FIGS. 2A and 2B.

FIG. 3 shows aspects of an exemplary working channel 220, which may have any of the properties of working channel 120 and may be used in conjunction with a distal tip, such as distal tip 100. Alternatively, working channel 220 may be used with alternative duodenoscopes. FIG. 2A shows a working channel 220, terminating in a proximal end 222. Lumen 224 may extend through a length of working channel 220, from proximal end 222 to a distal end of the working channel. Lumen 224 may be used to pass instruments from a port in a handle of a duodenoscope, through opening 130 in distal tip 110. Body fluids may also pass proximally through lumen 224 via opening 130.

Proximal end 222 of working channel 220 may include mating structure 226 that facilitates mating of working channel 220 with handle 12. For example, as shown in FIG. 3, mating structure 226 may include threads to provide for a screw fit between working channel 220 and a receptacle in the handle, which may be in communication with port 40.

A wall 227 of working channel 220 may define one or more lumens 228 that extend longitudinally through wall 227. Lumens 228 may be defined by a circular surface. Alternatively, lumens 228 may have alternate shapes. For example, lumen 228 may include a slot that extends radially inward from an outer surface of working channel 220. Lumen 228 may be entirely enclosed or may include portions that are open to an outer surface of working channel 220.

Lumens 228 may be in addition to a central lumen for receiving/transmitting tools, suction, and body fluids/tissue. Lumens 228 may extend along a longitudinal axis of working channel 220 but may not be coaxial with a central longitudinal axis of working channel 220. Lumens 228 may surround the central lumen. Each of lumens 228 may extend from proximal end 222 to a distal end of working channel 220. Lumens 228 may be open at proximal end 222 and at the distal end of working channel 220. Wall 227 may define any suitable number of lumens 228. For example, as shown in FIG. 2, wall 227 may define four lumens 228. Lumens 228 may form passageways for wires and/or cables, conduits, and/or elevator control elements that extend from the handle, through shaft 18, and to distal tip 110 of the duodenoscope. For example, cables and/or wires for powering and/or controlling viewing element 102 and lighting element 104 and/or for receiving signals from viewing element 102. Water and/or air supplies may also pass through lumens 228. Conduits may pass through lumens 228 in order to supply water and/or air from the handle to the distal tip of the duodenoscope. Alternatively, water and/or air may travel directly through lumens 228 without an intermediate conduit structure passing through lumens 228.

By way of example, working channel 220 may include four lumens 228. A first of the four lumens 228 may be used for providing air or another fluid, and a second may be used for providing water or another fluid. A third lumen 228 may be used to carry a signal cable for a feed from viewing element 102. A fourth lumen 228 may be used to carry a power cable, which may power, e.g., viewing element 102, lighting element 104, and motors of distal tip 100 used to raise and lower elevator 110 and/or to rotate distal tip 100.

A receptacle in handle 12 may provide for automatic connections between elements passing through lumens 228 of working channel 220 and corresponding structures in handle 12. For example, screwing in working channel 220 into an appropriate receptacle may provide for electrical connection between controls in handle 12 and corresponding wires in lumens 228. In such an example, after backfeeding working channel 220 through shaft 18, proximal end 222 of working channel 220 may be seated in a receptacle of handle 12, providing a single step for forming connections between elements in lumens 228 with corresponding elements of handle 12. Alternatively, elements carried in lumens 228 may be separately connected to corresponding elements of handle 12 before or after proximal end 222 is secured to handle 12. For example, wiring carried in a lumen 228 may terminate proximally in a plug that may be inserted into a receptacle of handle 12.

Figure 4A:
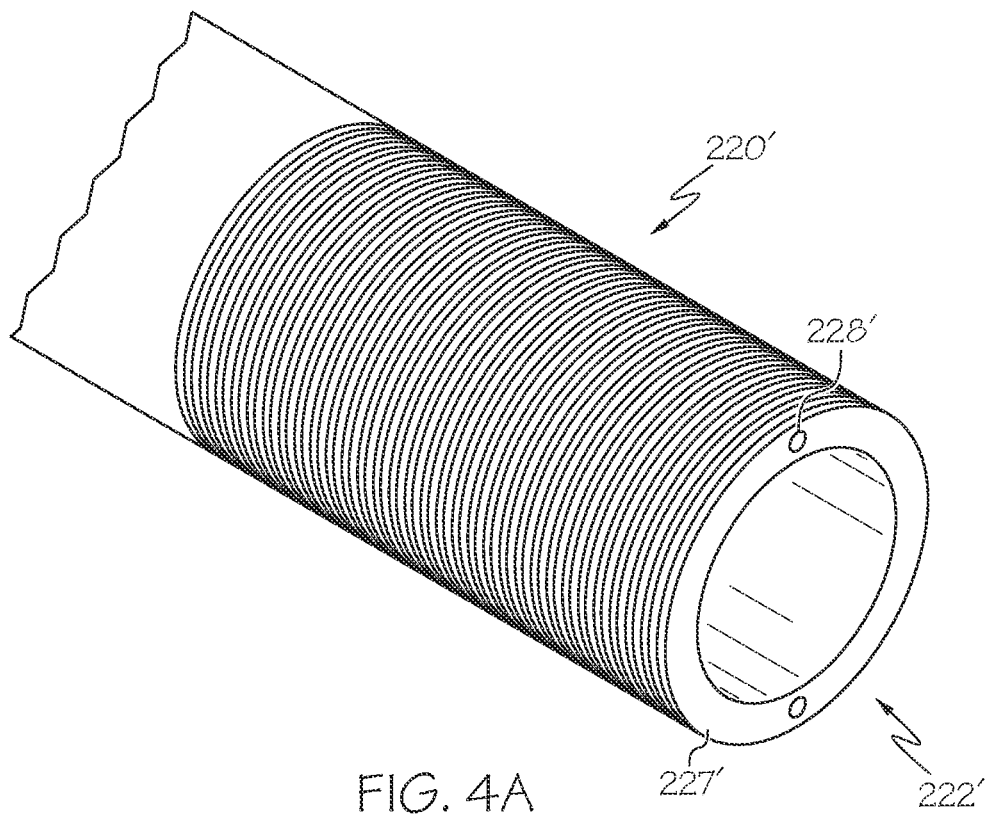
FIGS. 4A-4D show a distal tip and elements for use therewith.
Figure 4B:
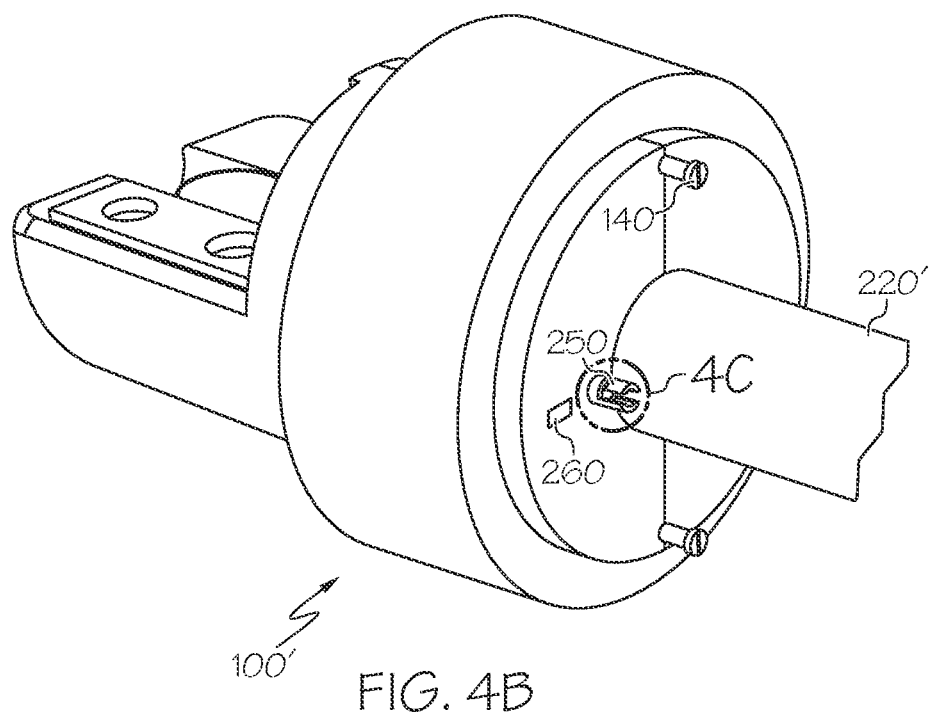

FIGS. 4A and 4B show an alternative distal tip 100' and an alternative working channel 220'. While distal tip 100' and working channel 220' are described together herein, features of distal tip 100' and/or working channel 220' may be combined with other aspects described herein. For example, features of distal tip 100 may be used alongside features of working channel 220', and features of distal tip 100' may be used alongside features of working channel 220. Distal tip 100' and working channel 220' may have any of the features of distal tip 100 and working channel 220, respectively, except where specified.

As compared to working channel 220, working channel 220' may have fewer lumens 228' formed therein. Instead of passing through lumens 228', some components may pass outside of working channel 220'. For example, working channel 220' may define two lumens 228'. The two lumens 228' may carry air (or another fluid) and water (or another fluid), respectively. Cables or wires for providing power and/or receiving an image signal from viewing element 102 may pass externally of working channel 220', through shaft 18. The cables or wires may extend through a port 260 on a proximal face of distal end 100'. Port 260 may be an opening, through which cables and/or wires may extend proximally from electronic elements (e.g., motors, viewing element 102, and/or lighting element 104). When distal tip 100' is positioned on shaft 18, the cable(s) and/or wire(s) may be backfed through shaft 18 and connected to a portion of handle 12. In such an example, port 260 may include sealing elements which prevent fluids (such as bodily fluids) from passing through port 260. Alternatively, port 260 may form a receptacle for receiving a connector. For example, single-use or reusable wire(s) and/or cable(s) may extend distally from handle 12 toward distal tip 110'. The wire(s) and/or cable(s) may be fixedly or removably coupled to elements of handle 12. The wire(s) and/or cable(s) may terminate distally in a connector which may be inserted into port 260 in order to form electrical connections with elements of distal tip 100'.

Figure 4C:
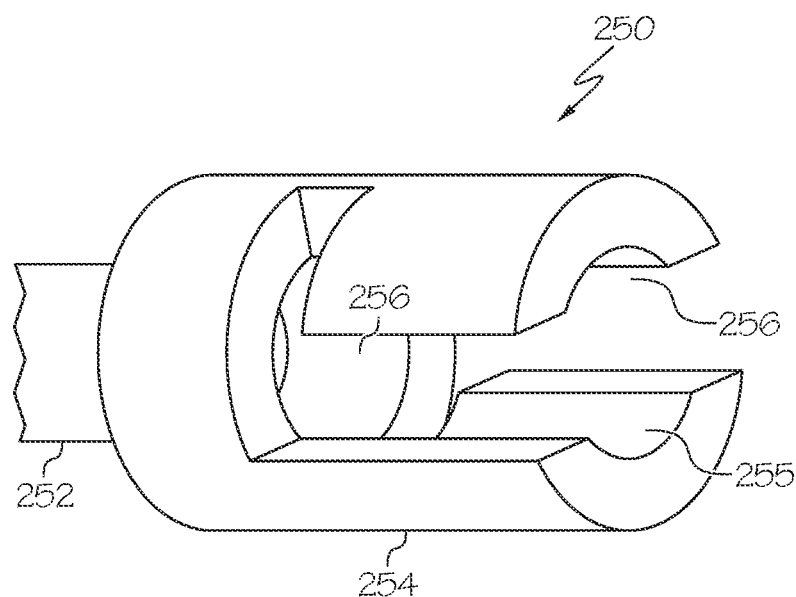
Figure 4D:
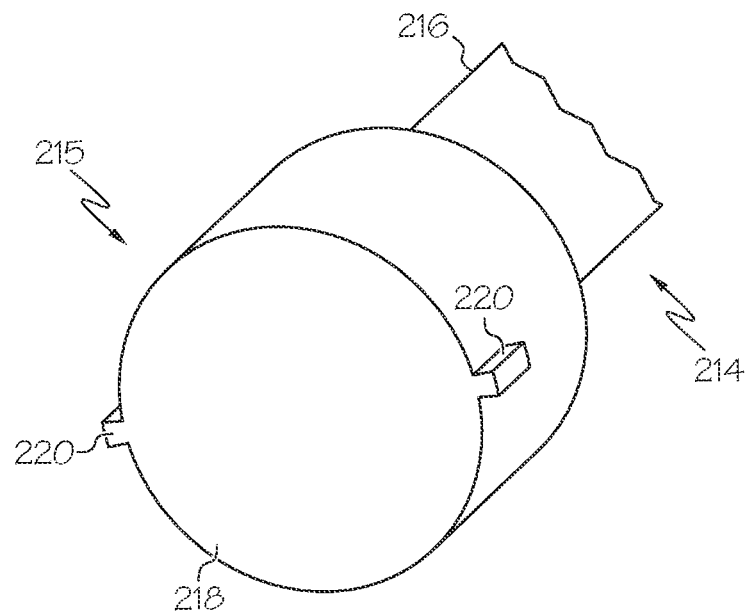

As described above with respect to distal tip 100, elevator 110 may be operated (raised or lowered) via a motor in distal tip 100. Alternatively, a control wire 214 (FIG. 4D) may be connected to elevator control lever 38 and may pass through shaft 18. Movement of elevator control lever 38 may cause proximal and distal motion of control wire 214. Control wire 214 may terminate in a distal end 215, shown in FIG. 4D. Distal end 215 may include a shaft 216 and a head 218. Head 218 may extend radially outward relative to shaft 216. One or more protrusions 220 may extend radially outward from a surface of head 218. For example, as shown in FIG. 4D, two protrusions 220 may extend from head 218. Protrusions 220 may have any suitable shape. For example, as shown in FIG. 4D, protrusions 220 may have a greater longitudinal dimension than a circumferential dimension (may extend further longitudinally along head 218 than circumferentially about head 218).

Control wire 214 may be operatively connected to a pin 250 extending proximally from a proximal face of distal tip 100'. Pin 250 may form a proximal end of a control wire extending within distal tip 100', which may be operatively connected to elevator 110, such that when pin 250 is moved proximally, elevator 110 raises, and when pin 250 is moved distally, elevator 110 lowers. Alternatively, pin 250 may be operatively connected to a separate control wire within elevator 110 such that the elevator raises and lowers as pin 250 is moved proximally and distally. FIG. 4C shows a detailed view of pin 250. Pin 250 may include a shaft 252 and a head 254 having a greater radial dimension than shaft 252. Alternatively, pin 250 may have a uniform radial dimension. Head 254 may define a cavity 255, which may be open on a proximal end of head 254. A portion of pin 250 (e.g., head 254) may define one or more slots 256. For example, as shown in FIG. 4C, pin 250 may define two slots 256 that extend through a wall of head 254. Slots 256 may be L-shaped. A distal portion of slot 256 may extend in a circumferential direction, while a proximal portion of slot 256 may extend in a longitudinal direction.

In order to operatively connect control wire 214 to pin 250, distal end 215, including head 218, may be inserted into cavity 255 with protrusions 220 aligned with slots 256. Distal end 215 may be moved distally so that protrusions 220 track along slots 256. Distal end 215 may then be rotated so that protrusions 220 continue to track along the portion of slot 256 that extends circumferentially about pin 250.

Control wire 214 may be coupled to pin 250 while pegs 140 are simultaneously (or subsequently or previously) coupled to features of shaft 18. For example, as distal tip 100' and shaft 18 are brought together, distal end 215 of control wire 214 may be inserted into cavity 255 of pin 250, and pegs 140 may be inserted into holes, slots, or other features of shaft 18. Distal tip 100' may then be twisted with respect to shaft 18. Twisting may cause control wire 214 and pin 250 to be coupled together, while coupling pegs 140 to shaft 18 to secure distal tip 100' with respect to shaft 18. Distal tip 100 or 100' may also be attached to shaft 18 via twisting, even if pin 250 is not present on distal tip 100'. A skirt may be positioned about distal tip 100/100' and shaft 18, in order to further secure distal tip 100/100' to shaft 18 and to inhibit fluid ingress and egress between distal tip 100/100' and shaft 18. After a procedure, a distal tip 100 or 100' may be detached from shaft 18 (e.g., via twisting in the opposite direction). Distal tip 100 or 100' may be disposable or may be reprocessed for a further procedure.

Although light emitting diodes have been discussed with respect to distal tips 100, 100', it will be appreciated that optical fibers may be used alternatively or additionally. Optical fibers may extend through shaft 18 and distal tip 100 or 100'. The optical fibers of shaft 18 and distal tip 100 or 100' may meet at a junction between shaft 18 and distal tip 100 or 100'. The optical fibers may be flush with a proximal surface of distal tip 100 or 100' and a distal surface of shaft 18. Flushness of the optical fibers may result in easier cleaning of components such as shaft 18, because fluids may not leak into crevices or adhere to outer surfaces of the optical fibers.

Figure 5A:
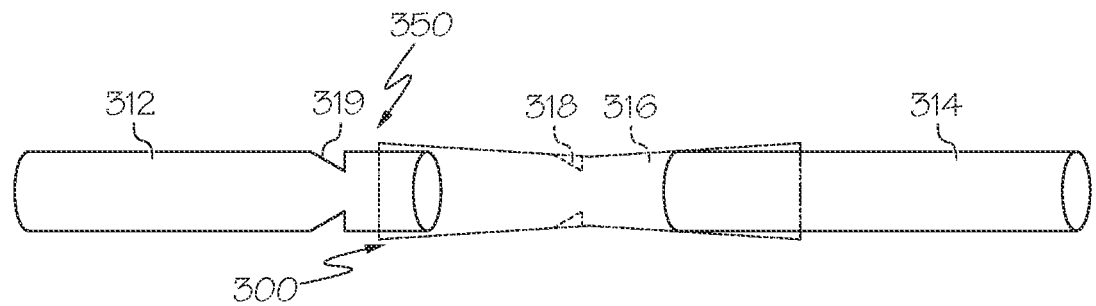
FIGS. 5A-5C show exemplary securing mechanisms.
Figure 5B:
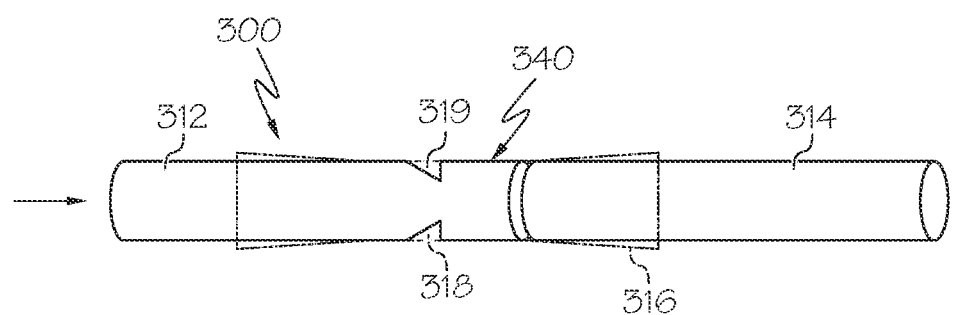
Figure 5C:
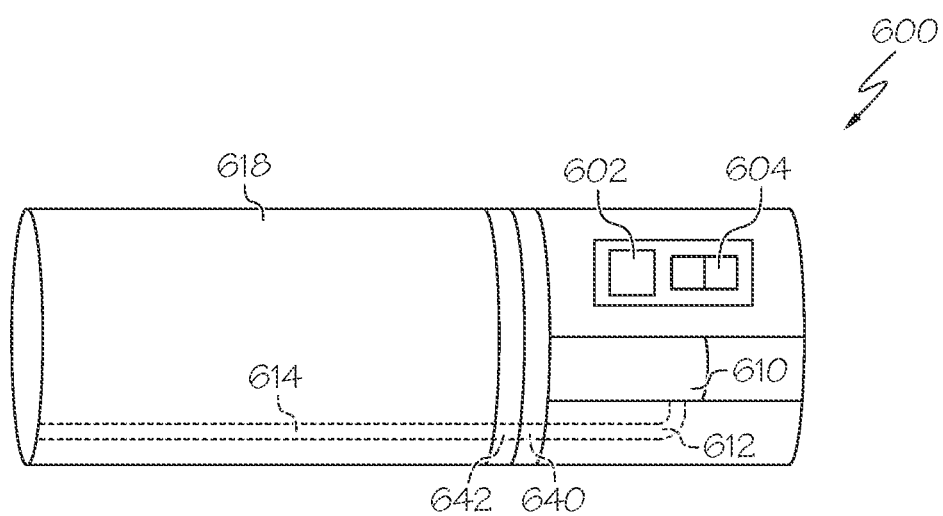

FIGS. 5A-5C show alternative attachment mechanisms for coupling a portion of a control wire in shaft 18 to a portion of a control wire in a distal tip, such as distal tip 100 or 100'. Although the attachment mechanisms described in FIGS. 5A-5C may be described with respect to control wires for raising and lowering an elevator, it will be appreciated that the attachment mechanisms may additionally or alternatively be used to fix a distal tip (such as distal tip 100 or 100') to shaft 18.

FIGS. 5A-5B show a fixation mechanism 300, which may function like a finger trap. A distal tip control wire 312 may connect to an elevator (e.g., elevator 110) and may extend proximally through a distal tip toward shaft 18. A shaft control wire 314, which may extend through shaft 18, may have a sleeve 316 fixed thereabout. Sleeve 316 may define a lumen and may extend circumferentially around a distal portion of shaft control wire 314, which may be disposed within the lumen.

One or more protrusions 318 may extend radially inwardly from an inner surface of sleeve 316. One or more notches 319 may be formed in distal tip control wire 312. A single protrusion 318 may extend around an inner circumference of sleeve 316, and a single notch 319 may extend around a circumference of distal tip control wire 312. Alternatively, there may be multiple, discrete protrusions on sleeve 316 and multiple, discrete notches on distal tip control wire 312.

Protrusion 318 and notch 319 may have the same or complementary shapes, such that protrusion 318 may engage notch 319 in order to retain distal tip control wire 312 within sleeve 316 when distal tip control wire 312 is inserted into sleeve 316, and protrusion 318 is aligned with notch 319. For example, proximal sides of protrusion 318 and notch 319 may be approximately perpendicular to a longitudinal axis of shaft control wire 314, sleeve 316, and/or distal tip control wire 312. Distal sides of protrusion 318 and notch 319 may be angled radially outward/tapered toward the first side. Protrusion 318 and notch 319 may have triangular or wedge shapes.

FIG. 5A shows distal tip control wire 312 and shaft control wire 314, before distal tip control wire 312 is fully inserted into sleeve 316. In order to couple distal tip control wire 312 to shaft control wire 314, a proximal end of distal tip control wire 312 may be inserted into sleeve 316. Distal tip control wire 312 may be moved proximally. Distal tip control wire 312 may contact and deflect protrusions 318 radially outward. Sleeve 316 and/or protrusion 318 may be formed of material that is resilient, flexible, and/or has shape memory properties and is capable of flexion to allow a proximal end of distal tip control wire 312 to pass protrusion 318. As shown in FIG. 5B, protrusion 318 may engage notch 319 to retain distal tip control wire 312 within sleeve 316. Pulling distal tip control wire 312 distally with sufficient force may cause distal tip control wire 312 to disengage with sleeve 316 without destroying sleeve 316.

Although sleeve 316 has been described as being fixed around shaft control wire 314, sleeve 316 may alternatively be fixed around distal tip control wire 312, and shaft control wire 314 may include one or more notches, similar to notches 319. Although protrusions 318 have been described as extending radially inward from sleeve 316, it will be appreciated that protrusions 318 could extend radially outward from distal tip control wire 312 (or shaft control wire 314). Notches (similar to notches 319) could be formed in a wall of sleeve 316.

FIG. 5C shows an alternative mechanism for attaching a shaft 618 (having any of the properties of shaft 18) to a distal tip 600 (having any of the properties of distal tips 100, 100'). Distal tip 600 may include a viewing element 602 (which may have any of the properties of viewing element 102) and a lighting source 604 (having any of the properties of lighting source 104). Distal tip 600 may also include an elevator 610, which may have any of the properties of elevator 110. A shaft control wire 614 may extend through a length of shaft 618 and may have any of the properties of shaft control wire 314. Shaft control wire 614 may be operatively connected to an actuator in a duodenoscope handle (such as handle 12) in order to move shaft control wire 614 proximally and distally. A distal tip control wire 612 may extend longitudinally through distal tip 600 and may be operatively connected to elevator 110, such that proximal and distal movement of distal tip control wire 612 may raise and/or lower elevator 110.

Distal tip control wire 612 may terminate proximally in a magnetic element 640. Magnetic element 640 may be formed of the same material as a remainder of distal tip control wire 612 or may be a separate piece from distal tip control wire 612 that is fixedly secured to distal tip control wire 612. Shaft control wire 614 may terminate distally in a magnetic element 642. Magnetic element 642 may be formed of the same material as a remainder of shaft control wire 614 or may be a separate piece from shaft wire 614 that is fixedly secured to shaft control wire 614. Portions of magnetic elements 640 and 642 that face one another may have opposite polarities, such that magnetic elements 640 and 642 are attracted to one another. A magnetic force between magnetic elements 640 and 642 may be calibrated so that magnetic elements 640 and 642 secure distal tip control wire 612 to shaft control wire 614. After use, a sufficient force by a user may be used to separate magnetic element 640 from magnetic element 642. Alternatively, at least one of magnetic elements 640 and 642 may be electromagnetic and capable of being turned off to release magnetic element 640 from magnetic element 642. Alternatively, a key or other device may be configured to release magnetic elements 640 and 642 following use.

Figure 6A:
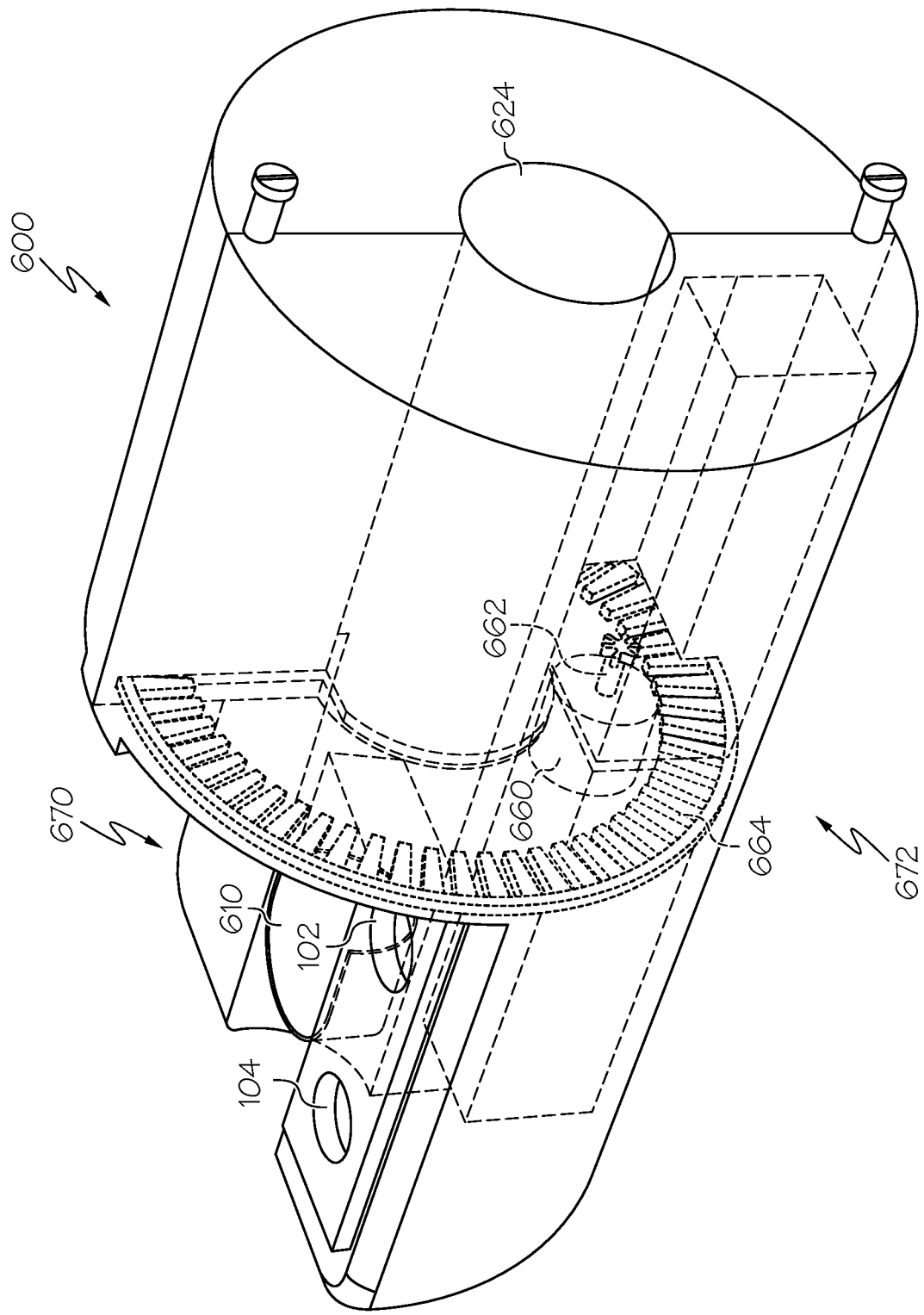
FIGS. 6A-7C depict exemplary rotation elements.
Figure 6B:
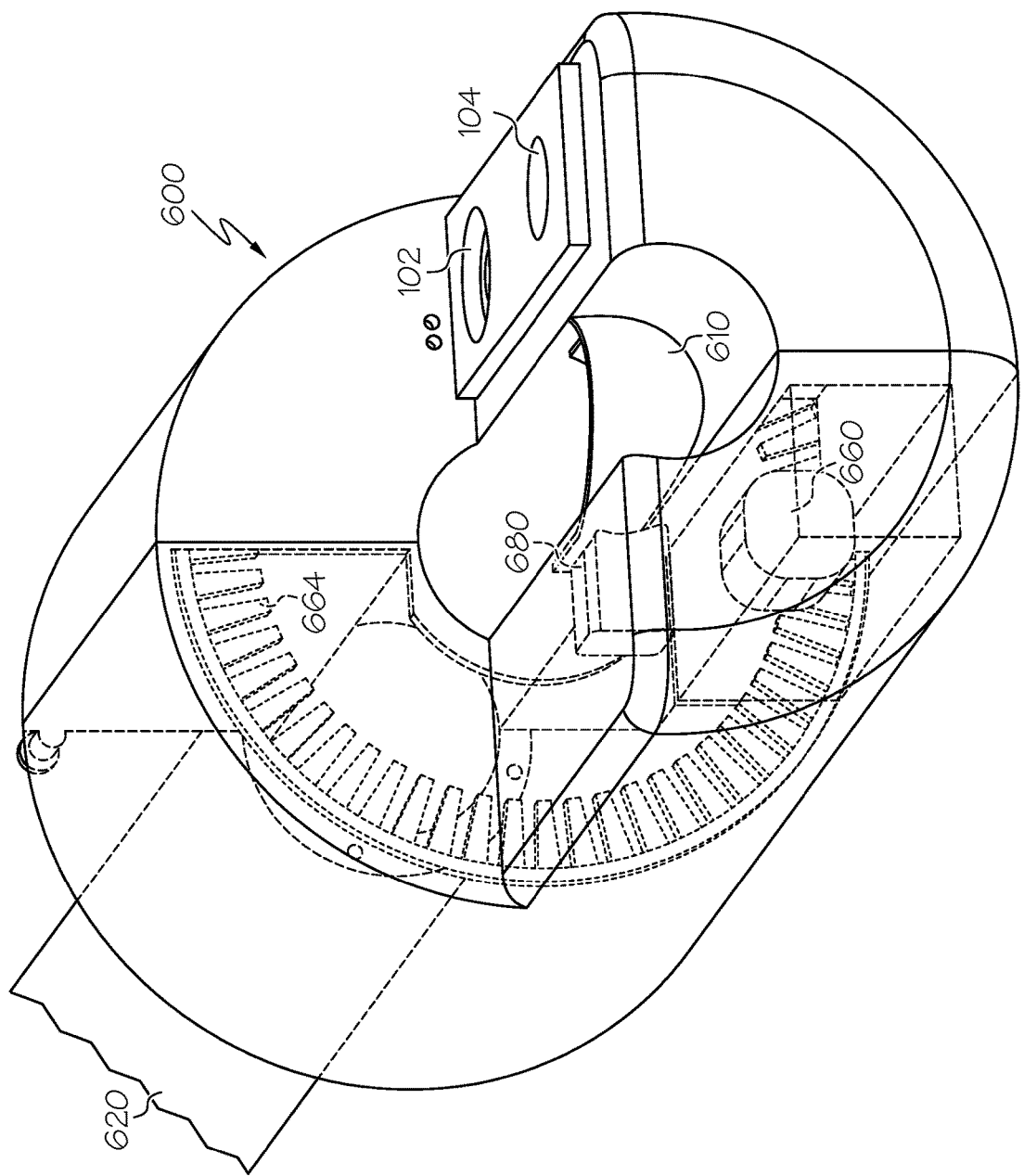

FIGS. 6A and 6B depict transparent views of an exemplary distal tip 600, which may have any of the features of the distal tips described above. Distal tip 600 may define a lumen 624 passing longitudinally therethrough. Lumen 624 may lead from a proximal opening on a proximal face of distal tip 600 to a distal opening. The distal opening of lumen 624 may lead to an elevator 610. Elevator 610 may have any of the features of the elevators described above. Elevator 610 may be configured to raise and lower in order to change an orientation of an instrument passing through lumen 624 and out of a distal end of lumen 624. As shown in FIG. 6B, a working channel 620 may be received within lumen 624. Working channel 620 may have any of the properties of working channels 120, 220, 220', described above. For example, working channel 620 may have the properties of working channel 220.

Distal tip 600 may include a rotation motor 660. Rotation motor 660 may be powered by, for example, a built in power source (e.g., a lithium ion battery), a wire or cable passing through a lumen of working channel 620, as described above, with respect to working channel 220. Rotation motor 660 may power a gear 662. Rotation motor 660 may cause gear 662 to rotate in a first direction or in a second direction. Gear 662 may have teeth formed around at least a portion of a circumference of gear 662.

Gear 662 may engage with teeth 664, which may extend radially inward from an inner circumferential surface of distal tip 600. Teeth 664 may function similarly to a rack gear but may be curved to correspond to a circumference of distal tip 600. As gear 662 rotates, gear 662 may engage with teeth 664 to cause rotation of a rotatable portion 670 of distal tip 600 relative to a stationary portion 672 of distal tip 600. Rotatable portion 670 may be distal to stationary portion 672. As shown, rotation motor 660 and gear 662 may be disposed in rotatable portion 670, and teeth 664 may be stationary (non-rotating), such that operation of rotation motor 660 causes rotatable portion 670, along with rotation motor 660, to rotate abut a longitudinal axis of distal tip 600 and/or lumen 624 (since teeth 664 are radially arranged about that axis). Alternatively, rotation motor 660 and gear 662 may be disposed in stationary portion 672, and teeth 664 may be disposed in rotatable portion 670, such that rotation of teeth 664 causes rotation of rotatable portion 670.

Teeth 664 may extend around an entirety of a circumference of distal tip 600, to allow approximately 360-degree rotation of rotatable portion 670. Alternatively, as shown, teeth 664 may extend around only a portion of a circumference of distal end 600, to allow less than 360-degree rotation (e.g., approximately 90 degree, approximately 180 degree, or approximately 270 degree rotation). Stops may be disposed at ends of rotation (e.g., on an inner circumference of distal tip 600) to limit rotation to the amounts described above. Rotatable portion 670 may be coupled to stationary portion 672 via, e.g., a bearing unit such as a polymer bearing unit.

Distal tip 600 may also include an elevator motor 680 (see FIG. 6B). Elevator motor 680 may cause raising and lowering motion of elevator 610. Elevator motor may be powered by a wire, cord, or a cable, which may extend through a lumen of working channel 620 (e.g., as described with respect to working channel 220).

Although rotation motor 660, gear 662, teeth 664, and elevator motor 680 are described with particular respect to disposable distal tips, such as those described above, it will be appreciated that those elements may be used with a variety of distal tips of duodenoscopes or other types of endoscopes.

Figure 7A:
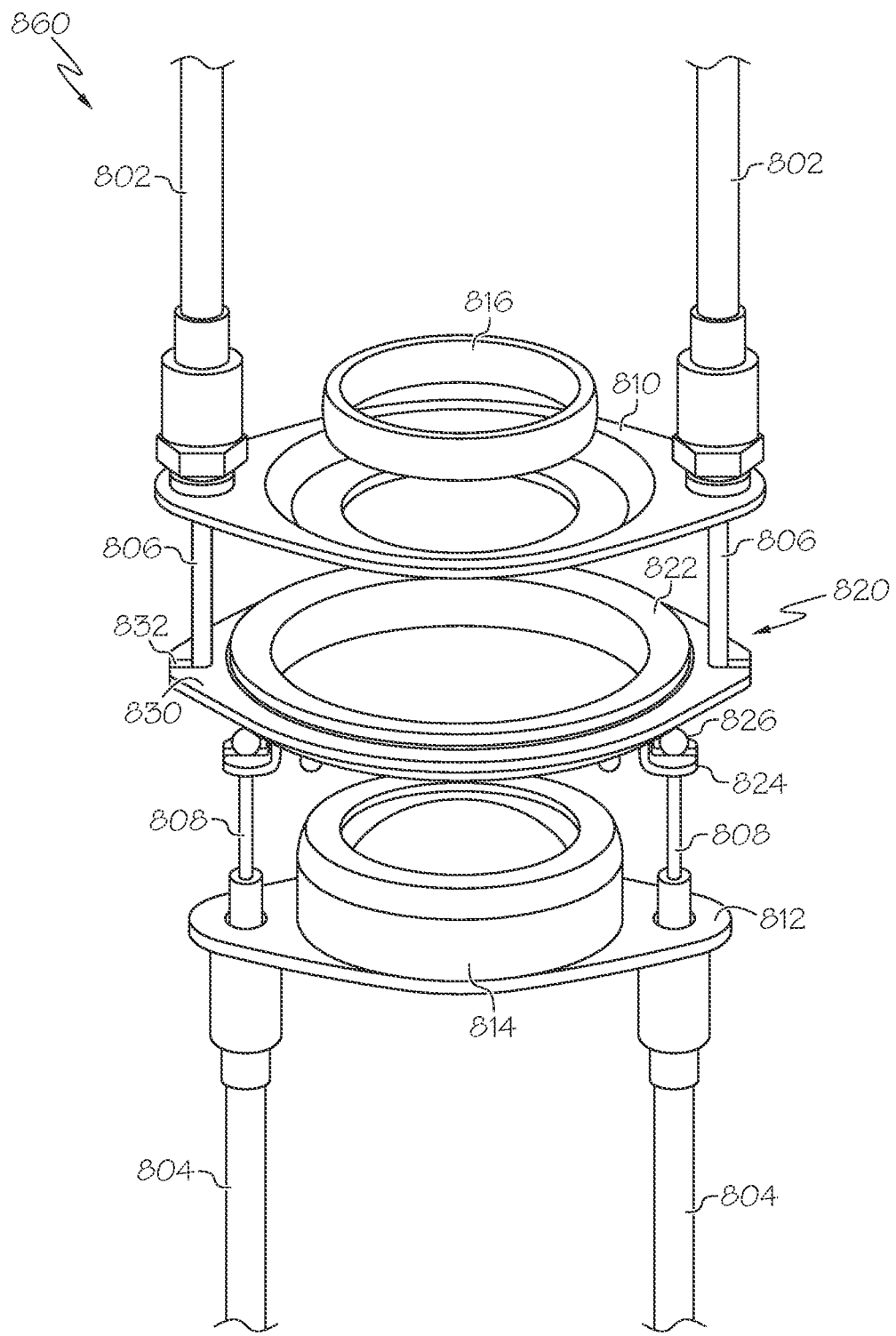
Figure 7B:
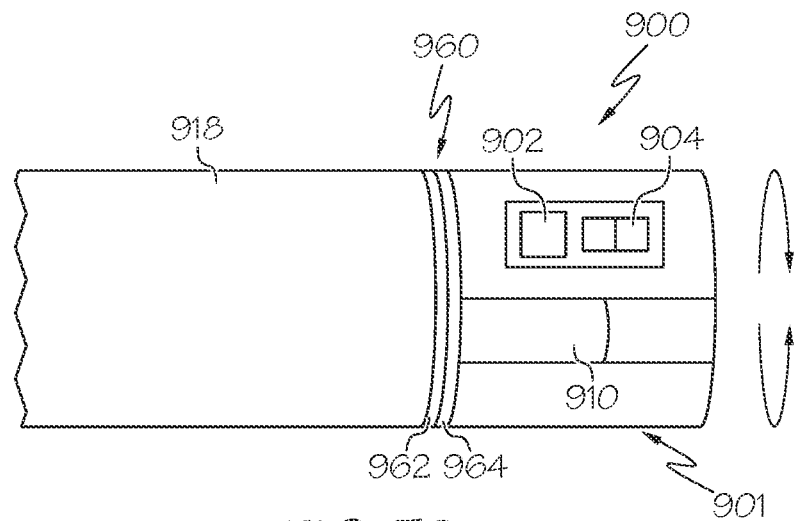

FIGS. 7A and 7B depict components that may be used to facilitate rotation of a distal tip of duodenoscope 10 relative to shaft 18 of duodenoscope 10. The components of FIGS. 7A and 7B may be used along with the distal tips described herein or with alternative distal tips.

FIG. 7A depicts a detangler 860, that may be used to assist in inhibiting twisting and tangling of components such as wires or cables extending between a rotating portion (e.g., a distal tip) of a duodenoscope or other endoscope and a non-rotating portion (e.g., a shaft) of the duodenoscope or other endoscope.

For example, cables 804 may extend through a shaft, such as shaft 18. Cables 804 may extend through or be fixed to a plate 812. Alternatively, plate 812 may be omitted. Plate 812 may be a portion of a distal end of the shaft (e.g., a distal face of the shaft). Distal portions 808 of cables 804 may extend distally of plate 812. As shown in FIG. 7A, cables 804 may be Bowden cables. Distal portions 808 of cables 804 may lack an outer covering or sheath of more proximal portions of cables 804 where cables 804 are Bowden cables. Alternatively, cables 804 may be other types of cables or wires, and distal portions 808 may be uniform to a remainder of cables 804. Although two cables 804 are shown, it will be appreciated that other numbers of cables 804 (e.g., four) may be used.

A distal end of cables 804 may be coupled to a detangling element 820. Detangling element 820 may include a plate 830 and a ring 822. Ring 822 may be received within opening of plate 830 and may be rotatable relative to plate 830. A rim of ring 822 may be on a distal side of plate 830. Ball bearings may be disposed between ring 822 and plate 830 in order to ease rotation between ring 822 and plate 830. Ring 822 may have arms 824 that extend proximally, through the opening of plate 830. Arms 824 may define slots for receiving cables 804 (e.g., for receiving distal portions 808). A distal end of cables 804 may include a cap 826 (e.g., a rounded, protruding end of cables 804) to retain each of cables 804 within the slots of arms 824.

Cables 802 may extend through a distal tip of a duodenoscope or other endoscope (such as any of the distal tips described herein). Cables 802 may extend through or may be fixed to a plate 810. Alternatively, plate 810 may be omitted. Plate 810 may be a portion of a distal tip (e.g., a proximal face of the distal tip). Proximal portions 806 of cables 802 may extend proximally of plate 810. As shown in FIG. 7A, proximal cables 802 may be Bowden cables, and proximal portions 806 may include wires or cables of the Bowden cables without an exterior sheath/covering. Although two cables 802 are depicted, it will be appreciated that alternative numbers (e.g., four) cables may be utilized.

Plate 830 of detangling element 820 may define slots 832 for receiving cables 802 (such as proximal portions 806). A proximal end of cables 804 may include a cap (e.g., a rounded, protruding end of cables 802, which may have any of the properties of cap 826) to retain each of cables 802 within the slots of plate 830.

Because ring 822 may be rotatable relative to plate 830, cables 802 may be rotated about an axis of detangling element 820 without rotating cables 804, thereby avoiding tangling of cables 804 (or cables 802) due to twisting of the cables. Detangling element 820 may have properties (e.g., conductivity) or may have features (e.g., traces) that allow communication of cables 804 and cables 802, via detangling element 820. Alternatively, cables 802, 804 may be articulation wires/cables that allow steering of a distal end of the shaft. Where the cables 802, 804 are articulation wires, it will be appreciated that additional cables may also be utilized so as to provide up/down/left/right articulation. Additional cables may have properties like those of cables 802, 804 and may interface with detangling element 820 in similar manners.

Detangler 860 may also include rings 814 (on a sheath side of detangling element 820) and rings 816 (on a distal tip side of detangling element 820), which may facilitate installation of detangler 860 and may mate with elements of the duodenoscope and/or the detangler 860. For example, ring 814 may fit in a central opening of ring 822 and may be fixed to plate 812. In such a configuration, ring 814 may facilitate positioning of plate 812 relative to detangling element 820. Ring 814 may additionally or alternatively form seals.

Only some aspects of a detangler 860 may be used along with the duodenoscope or other endoscope. For example, detangling element 820 (or a similar structure having the same or similar functions) may be used, but plates 812 and 810 may be omitted. Detangler 860 may be used in conjunction with other aspects described herein (e.g., with the motors of distal tip 600 of FIGS. 6A and 6B).

Figure 7C:
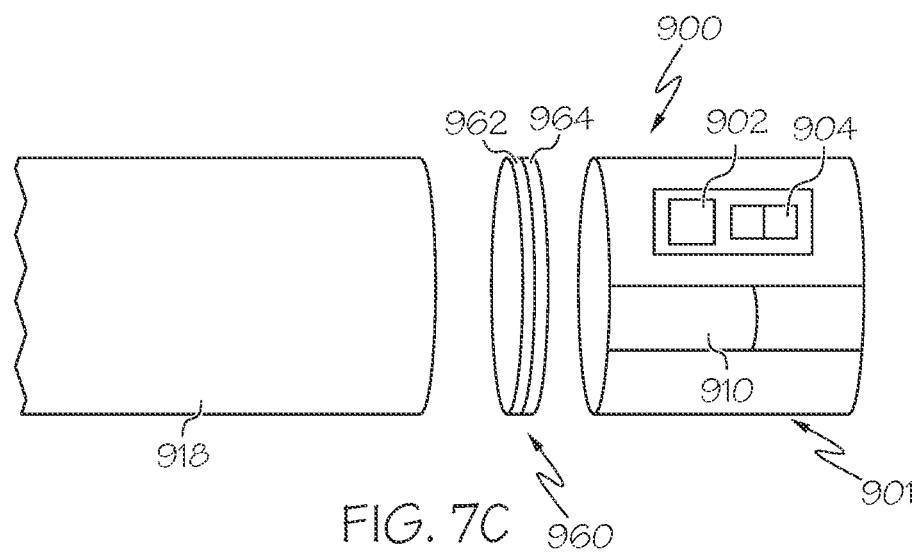

FIGS. 7B and 7C show aspects of a duodenoscope 900 that may have rotation features, which may be used in conjunction with detangler 860 or distal tip 600 or with other elements described herein. FIG. 7C shows an exploded view of the device of FIG. 7B. Duodenoscope 900 may include a shaft 918, which may have any of the properties of the shafts described herein (e.g., shaft 18). Duodenoscope 900 may have a distal tip 901 having any of the properties of the distal tips described herein. Distal tip 901 may have a viewing element 902 and a lighting element 904, having any of the properties of the other viewing elements and lighting elements described herein. Distal tip 901 may also have an elevator 910, having any of the features of the elevators described herein.

Distal tip 901 may be joined to shaft 918 via a rotation bearing 960. Rotation bearing 960 may include a stationary plate 962 and a rotating plate 964, which may be detachable from one another. Rotating plate 964 may rotate 360 degrees (or less than 360 degrees) relative to stationary plate 962. Rotation bearing 960 may be used with any of the exemplary distal tips described herein in order to facilitate rotation of the distal tip relative to a duodenoscope shaft or vice versa. Rotation bearing 960 may be, for example, a lazy Susan-type bearing. Rotation bearing 960 may have any of the properties of detangling element 820, described above, which also includes two components (plate 830 and ring 822) that are rotatable relative to one another. Cables may be secured to rotation bearing 960 in a similar manner to detangler 860, described above. For example, cables of shaft 918 may be secured to stationary plate 962, and cables of distal tip 901 may be secured to rotating plate 964.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device, comprising:
    a distal tip having:
        a viewing element,
        a lighting element,
        at least one mating component configured to removably couple the distal tip to a shaft, and
        an elevator control wire for raising and lowering an elevator of an endoscope, wherein a proximal end of the elevator control wire is at a distal end of the medical device and includes a notch configured to mate with a protrusion of a sleeve that extends around a distal portion of a shaft elevator control wire;
    a working channel fixedly coupled to the distal tip and defining a central lumen configured to receive a tool, wherein a wall of the working channel defines at least one additional lumen, and wherein the working channel is configured to be removably inserted into the shaft; and
    at least one of a wire, a cable, or a conduit passing through the at least one additional lumen.

2. The medical device of claim 1, wherein at least one of the wire, the cable, or the conduit includes the wire or the cable, and wherein the wire or the cable is configured to operate at least one of an elevator of the distal tip, the viewing element, or the lighting element.

3. The medical device of claim 2, wherein the distal tip further includes a motor operative to raise or lower the elevator.

4. The medical device of claim 3, wherein at least one of the wire, the cable, or the conduit includes the wire or the cable, and wherein the wire or the cable is configured to provide power to the motor.

5. The medical device of claim 1, wherein the wall of the working channel defines at least two additional lumens.

6. The medical device of claim 1, wherein the at least one mating component includes at least one peg extending from a proximal surface thereof.

7. The medical device of claim 1, wherein the distal tip is configured to be rotatable relative to the shaft.

8. The medical device of claim 1, wherein the distal tip includes a motor configured to rotate the distal tip relative to the shaft.

9. The medical device of claim 8, wherein the motor is configured to rotate a gear, and wherein the distal tip includes teeth configured to engage with the gear.

10. The medical device of claim 1, wherein a proximal end of the working channel includes a plurality of threads for securing the proximal end to a handle at a proximal end of the shaft.

11. The medical device of claim 1, wherein a proximal end of the distal tip defines a port for operatively connecting an electronic element of the distal tip to one of the wire, the cable, or the conduit extending through the shaft.

12. A method comprising:
    detachably coupling a distal tip to a shaft of a medical device, the distal tip having:
        a viewing element, and
        a lighting element;
    feeding a working channel, coupled to the distal tip, through the shaft from a distal end of the shaft to a proximal end of the shaft, wherein a proximal portion of the working channel includes a plurality of threads,
    detachably coupling the proximal portion of the working channel to a handle of the medical device via the plurality of threads; and
    at a distal end of the medical device, detachably coupling a notch of an elevator control wire to a protrusion of a sleeve that extends around a distal portion of a shaft elevator control wire, wherein the elevator control wire raises and lowers an elevator of the medical device.

13. The method of claim 12, wherein the working channel defines a central lumen configured to receive a tool, wherein a wall of the working channel defines at least one additional lumen, wherein at least one of a wire, a cable, or a conduit passes through the at least one additional lumen, wherein at least one of the wire, the cable, or the conduit is configured to be operatively connected to at least one of the viewing element, the lighting element, or a nozzle.

* * * * *